United States Patent [19]

Negishi et al.

[11] Patent Number: 5,380,422
[45] Date of Patent: Jan. 10, 1995

[54] MICRO-ELECTRODE AND METHOD FOR PREPARING IT

[75] Inventors: Akira Negishi, Matsudo; Hiroko Kaneko, Tsukuba; Takamasa Kawakubo; Yoshihisa Suda, both of Fujioka, all of Japan

[73] Assignees: Agency of Industrial Science and Technology; Mitsubishi Pencil Kabushiki Kaisha, both of Tokyo, Japan

[21] Appl. No.: 905,768

[22] Filed: Jun. 29, 1992

[30] Foreign Application Priority Data

Jul. 18, 1991 [JP] Japan ................................. 3-202138

[51] Int. Cl.$^6$ ............................................. G01N 27/26
[52] U.S. Cl. ..................................... 204/403; 204/416; 204/418; 204/433; 204/435; 204/294
[58] Field of Search ............... 204/412, 433, 435, 403, 204/416, 418, 419, 422, 294

[56] References Cited

U.S. PATENT DOCUMENTS

| | | | |
|---|---|---|---|
| 3,709,810 | 1/1973 | Grubb et al. | 204/433 |
| 4,959,130 | 9/1990 | Josowicz et al. | 204/418 |
| 5,218,757 | 6/1993 | Kaneko et al. | 204/416 |
| 5,269,903 | 12/1993 | Ikariyama et al. | 204/403 |

FOREIGN PATENT DOCUMENTS

| | | |
|---|---|---|
| 63-78698 | 3/1989 | Japan. |
| 4-74957 | 3/1992 | Japan. |
| 4-74958 | 3/1992 | Japan. |

OTHER PUBLICATIONS

Extended Abstracts vol. II for 40th ISE (International Society of Electrochemistry) meeting held in Kyota, Japan Sep. 17–22, 1989 Kaneko et al., "Electrochemical Behavior of GRC Electrodes for Voltammetry".

Extended Abstracts vol. II for 40th ISE (International Society of Electrochemistry) meeting held in Kyota, Japan Sep. 17–22, 1989 Abe, et al., "Fabrication and Application of Micro–electrode to In-vivo Voltammetry".

Extended Abstracts vol. II for 40th ISE (International Society of Electrochemistry) meeting held in Kyota, Japan Sep. 17–22, 1989, Kaneko et al., "Redox Reactions of Vanadium Ions on GRC and Carbon Fiber Electrodes".

(List continued on next page.)

Primary Examiner—Kathryn Gorgos
Assistant Examiner—Bruce F. Bell
Attorney, Agent, or Firm—Darby & Darby

[57] ABSTRACT

A working micro-electrode with a reference electrode prepared by coating a working micro-electrode with an insulating material except a working electrode portion, forming a silver layer on the coated surface, and then changing a portion of the silver layer into silver chloride which is the reference electrode; a working micro-electrode with a reference electrode and a counter electrode prepared by coating the working micro-electrode with the reference electrode with an insulating material, and then forming the counter electrode on the surface of the insulating material; and methods for preparing these composite micro-electrodes.

Heretofore, even if the working electrode is thinly constituted, the merit of the micro-electrode has not been sufficiently utilized, since the reference electrode and the counter electrode have been thick. However, the present invention can solve this problem and can facilitate experiments in which the micro-electrode is necessary.

Since an inexpensive material such as carbon can be used, the working electrode may be constituted so as to be disposable or can be cut off the used portion to repeatedly obtain a new electrode surface. Therefore, the working electrode of the present invention is economical.

9 Claims, 4 Drawing Sheets

OTHER PUBLICATIONS

Treatise for Technical Journal Tanso (Carbon) No. 152, pp. 106–114, 1992, Kawakubo et al., "Electrochemical Behavior of Carbon Microelectrodes Prepared by Using Graphite/Carbon Composite" no month available.

Extended Abstracts for the 1991st year Autumn meeting of the Society of Electrochemistry held in Nagota Institute of Technology on Oct. 12–13, 1991. Negishi et al. "Micro Carbon Electrode with Reference Electrode".

Treatise for Technical Journal "Electrochemistry", No. 12, 60, pp. 1143–1145 (1992) Kaneko et al., Carbon Sensor Electrode Containing a Reactant in the Microholes no month available.

Treatise for "Science" 22 Apr. 1988 vol. 240, pp. 415–419, Wightman, Voltammetry with Microscopic Electrodes in New Domains.

Catalogue of Ecosse Sentors, Co. "Disposable Electrodes for Anodic Stripping Voltammetry" no month or year available.

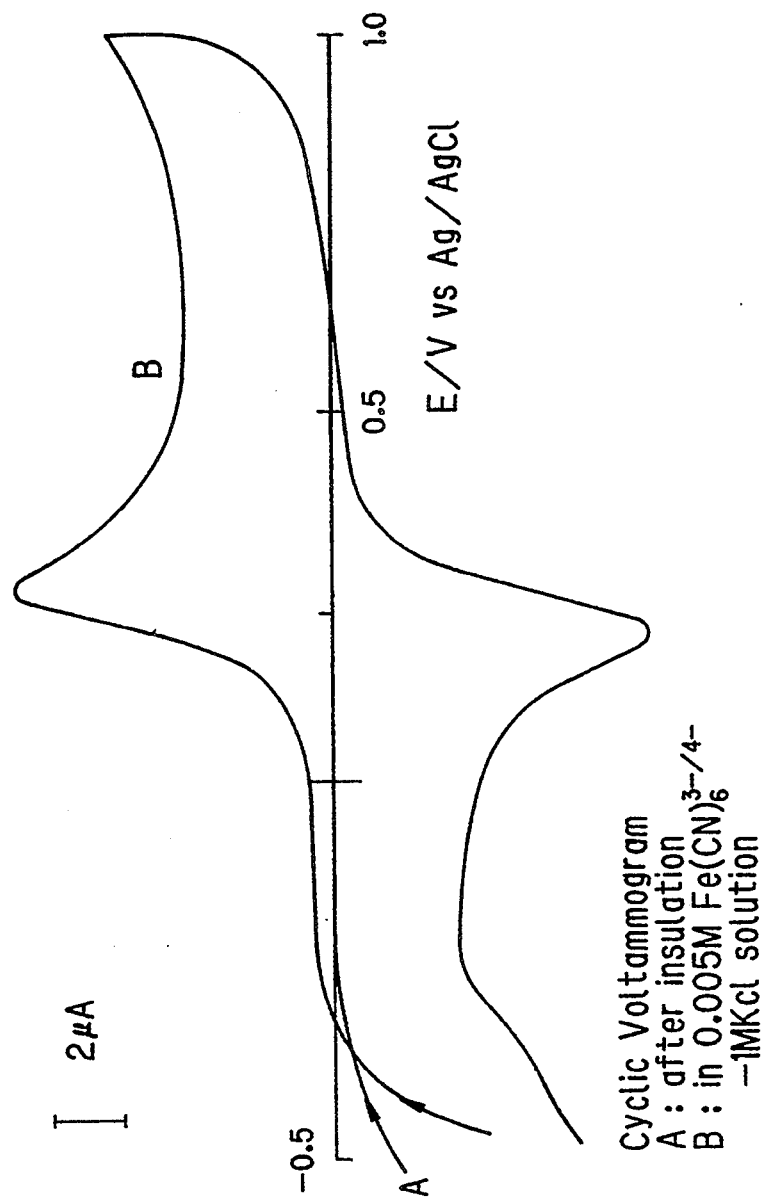

MICRO-ELECTRODE AND METHOD FOR PREPARING IT

BACKGROUND OF THE INVENTION (i) Field of the Invention

The present invention relates to a working micro-electrode with a reference electrode and a working micro-electrode with a reference electrode and a counter electrode. Each of the working micro-electrode with the reference and the working micro-electrode with the reference electrode and the counter electrode can be used as, for example, any one of all electrochemical detectors, environmental analysis sensors, pathologic inspection sensors, and probe electrodes which are for the detection of an organism, a food and the like, and which is severely required to be harmless and non-toxic. Furthermore, the present invention also relates to methods for preparing them.

(ii) Description of the Prior Art

An abbreviated rapid analysis using a sensor as a detecting means which has been promptly developed in recent years in many fields of an electrochemical determination has a very high selectivity and permits a high-sensitive measurement, and for this reason, this kind of abbreviated rapid analysis begins to be often used in the analysis and evaluation of clinical samples and environmental samples each containing a trace amount of a component to be determined and simultaneously many other kinds of compounds.

However, a working micro-electrode and a micro-sensor electrode have not been put into practice because of technical difficulty, except for a relatively large working electrode (diameter=about 10 mm) with a reference electrode, and a composite ion sensor with a reference electrode for measuring a hydrogen ion concentration and a metallic ion concentration which have been already practiced. Therefore, in the above-mentioned fields where measurement is made for a trace amount of a sample or in a micro-region, the employment of the thick reference electrode fairly reduces the merit of the working micro-electrode.

Lately, it has become very important to obtain biological information in vivo and in situ in a local site of an organism, for example, in a cell by the use of a sensor electrode capable of detecting such a specific material with a high sensitivity. For this purpose, it is required that the electrode is disposed in the vicinity of a target cell of the organism or thrust into the cell to give a physical, chemical or electrical irritation to the cell, so that a response material is released or a specific material chemically produced is selected to achieve its determination. Also for this purpose, it is fair to say that the assembly of the micro-electrode with the micro-reference electrode is a significant technique.

As such composite type measuring electrodes, a pH meter for determining hydrogen ions, an ion sensor for detecting inorganic ions such as sodium ions and the like, have been heretofore put into practice, as described above.

However, most of the composite electrodes cannot withstand a long-term use except for large composite electrodes (diameter=about 10 mm) such as the pH meter, the inorganic ion sensor and a metallic (mainly platinum) electrode for titration. That is, they have the drawback that a life is short. In particular, most of the composite electrodes in which a working electrode having a diameter of 1 mm or less is associated with a reference electrode and a counter electrode can scarcely withstand practical use.

SUMMARY OF THE INVENTION

The first object of the present invention is to provide a working micro-electrode with a reference electrode which comprises the micro-working electrode made of an inexpensive material is assembled with the simple reference electrode.

The second object of the present invention is to provide a working micro-electrode with a reference electrode and a counter electrode which comprises the above-mentioned working micro-electrode with a reference electrode is further associated with the counter electrode.

The third object of the present invention is to provide the above-mentioned electrodes which are disposable without taking care of its life and which have no difference of properties.

The fourth object of the present invention is to provide a composite micro-sensor electrode obtained by associating a reference electrode with a sensor in which a working electrode is impregnated, adsorbed or chemically modified with a reactant such as an enzyme, a metal complex compound, an organic compound or a metabolite to retain the desired reactant in the working electrode or on the surface thereof.

The fifth object of the present invention is to provide methods for preparing the above-mentioned electrodes.

More specifically, the present invention intends to provide a composite micro-electrode and a micro-sensor electrode mainly comprising this composite micro-electrode which permit detecting a specific substance and which meet the following requirements.

(1) Composing a reference electrode on the carbon micro-sensor electrode of a cellular scale which can give all of current, voltage and mechanical irritation to an organism.

(2) Not poisoning a measuring system, being safe even if the electrode remains in vivo, and being usable in the inspection of foods.

(3) Having such mechanical strength as to permit the electrochemical inspection of an extremely small region of an organism or a food by thrusting the electrode into the small region.

(4) Having less uneven sensor characteristics, and providing the reproductivity of data and reliable determination.

(5) Being capable of stably measuring an electrode reaction by rapid coating, polishing or the like without requiring a special pretreatment and aftertreatment.

(6) Being inexpensive and disposable.

That is, aspects of the present invention are as follows.

(1) A working micro-electrode with a reference electrode comprising a working micro-electrode, an insulating layer coated on said working micro-electrode except a working electrode portion and a reference electrode formed on said insulating layer.

(2) A working micro-electrode with a reference electrode and a counter electrode according to the preceding paragraph (1), further comprising an insulating layer on said reference electrode and a counter electrode formed on said insulating layer.

(3) The composite micro-electrode according to the preceding paragraph (1) or (2), comprising the material of the working micro-electrode being one selected from the group consisting of a metal, an alloy, carbon and a conductive polymer.

(4) The composite micro-electrode according to the preceding paragraph (3) comprising the carbon material which is used as the material of the working micro-electrode being a composite carbon thin wire or thin plate.

(5) The composite micro-electrode according to the preceding paragraph (4) comprising the crystalline carbon fine powder which is the material of carbon for the working electrode being at least one selected from the group consisting of graphite whisker, highly oriented pyrolytic graphite, Kish graphite, natural graphite and artificial graphite.

(6) The composite micro-electrode according to the preceding paragraph (4) comprising the organic binder which is the material of carbon for the working electrode being an organic compound which leaves a carbonized carbon when calcined in the inert atmosphere or the non-oxidizing atmosphere, and said organic compound being at least one selected from the group consisting of an organic polymer, its monomer or oligomer; a tar, a pitch, a carbonized pitch; a thermoplastic resin, and a polymer of a thermosetting resin.

(7) The composite micro-electrode according to the preceding paragraph (1) or (2) comprising the insulating material with which the micro-electrode is coated being a low-viscosity liquid state at room temperature, or being soluble in a solvent and being solidified after the removal of the solvent by a slight heat treatment or a catalytic action to show an insoluble or an infusible state.

(8) The composite micro-electrode according to the preceding paragraph (7) comprising the insulating material for the coating being at least one selected from the group consisting of a silicon resin, a polyimide resin, a methacrylic resin, and another type of initial polymers thereof.

(9) The composite micro-electrode according to the preceding paragraph (1) or (2) comprising the insulating material for the coating being an oxide insulating material containing glass.

(10) The composite micro-electrode according to the preceding paragraph (1) or (2) comprising said carbon micro-electrode having micro-pores thereon and therein impregnated with at least one insulating material selected from the group consisting of silicone oil, a glass-like resin, a polyimide resin, or at lease one reactant selected from the group consisting of a stable enzyme, a metal complex compound, an organic compound and a metabolite; coating layer outside of the electrode made from an insulating material; a pair of a silver film and a silver chloride film forming reference electrode.

(11) A method for preparing a working micro-electrode with a reference electrode which comprises the steps of coating the working micro-electrode with an insulating material except a working electrode portion; forming a silver film on the insulating material-coated surface, and then changing a part of the silver film into silver chloride to form the reference electrode, thereby obtaining the composite electrode.

(12) A method for preparing a working micro-electrode with a reference electrode and a counter electrode which comprises the steps of further coating the working micro-electrode with the reference electrode prepared in the preceding paragraph 11 with an insulating material, and then coating the surface of the resultant insulating film with a conductor to form the counter electrode thereon.

(13) The method for preparing a composite micro-electrode according to the preceding paragraph (11) which comprises the steps of preparing a composition comprising highly dispersing and mixing a crystalline carbon fine powder with an organic binder, extruding said composition into a desired thin wire or thin plate; and thermally treating at a temperature of 500° to 1500° C. in an inert atmosphere or a non-oxidizing atmosphere to form the working electrode comprising the resultant carbon thin wire or plate.

(14) The method for preparing a composite micro-electrode according to the preceding paragraph (13) further comprising the carbon thin wire or plate being further heated up to 1500° to 3000° C. in the inert atmosphere to achieve a graphite formation treatment, thereby obtaining the working electrode.

(15) The method for preparing a composite micro-electrode according to the preceding paragraph (9) wherein the oxide insulating material being formed by one method selected from the group consisting of a vapor deposition method, a sputtering method and a chemical vapor deposition method and another dry (deposition) method.

(16) The method for preparing a composite micro-electrode described in the preceding paragraph (11) wherein the formation of the silver film on the surface of the insulating film is achieved by any method selected from the group consisting of vapor deposition, sputtering and another dry (deposition) method, plating and another wet (deposition) method.

BRIEF DESCRIPTION OF THE DRAWINGS

FIG. 4 shows current/potential curves in 1M (mol dm$^{-3}$) potassium chloride-0.005M potassium ferrocyanide [$K_4Fe(CN)_6$] solution on the composite micro-electrode as shown in FIG. 2.

Figure 1:
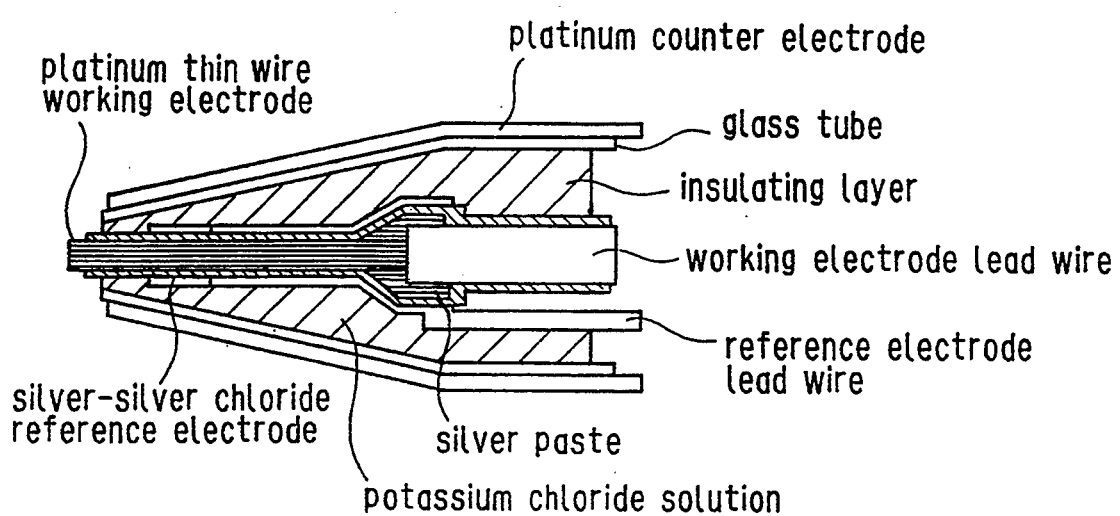
FIG. 1 is a constitutional view of a working micro-electrode with a reference electrode and a counter electrode obtained by forming the silver-silver chloride reference electrode on an insulating film of the working electrode comprising a platinum electrode thin wire (0.3 mm$\phi$), covering it with a glass tube, placing a potassium chloride solution in the glass tube, and then forming a platinum film on the outer periphery of the tube.

The curve A is a curve by which it has been confirmed that the carbon electrode is in an insulating state in the 1M potassium chloride, and the curve B is a current/potential curve measured in 1M potassium chloride-0.005M potassium ferrocyanide solution.

DETAILED DESCRIPTION OF THE PREFERRED EMBODIMENTS

The present inventors have intensively researched to solve the above-mentioned problems.

In the first place, in a composite electrode comprising a working electrode and a reference electrode, the requirements which the working electrode should meet are as follows:

(1) Having a large potential domain and a small blank current.
(2) Being excellent in reproductivity, and being capable of repeatedly using.
(3) Providing an active electrode reaction.
(4) Having uniform electrode properties.
(5) Containing less impurities, and not interfering with the electrode reaction.
(6) Easy handling and pretreatment.
(7) Not poisoning a measuring system.
(8) Excellent stability.

Inventors have accomplished the present invention as a results of researching the electrodes which meet these necessary conditions and method for preparing the same.

In the composite micro-electrode of the present invention, the material of the working electrode may be any one of conductive materials such as metals, alloys, carbon and conductive polymers, and the shape of the working electrode may be any one of a linear form, a spherical form, a plate form and a combination thereof. The employment of carbon is preferable, and this reason is as follows: Carbon is chemically stable and inexpensive, has micro-pores and a large conductive area, and permits impregnating the micro-pores with a reactant. Therefore, by the utilization of these features of carbon, the used portion of the working electrode can be cut off to advantageously supply a new electrode surface again and again.

In the case of the composite micro-electrode which can be used in the micro-sensor, a porous carbon thin wire having the micro-pores extending to its interior and surface is used which is impregnated with a reactant such as an enzyme, a metal complex compound, an organic compound or a metabolite.

The composite micro-electrode or the micro-sensor having the above-mentioned material and shape is then insulated except its working electrode portion in the undermentioned manner. In the case that the electrode has the linear shape, the whole electrode is insulated and its tip is then cut, whereby it can be used as a disk-type electrode. Therefore, in this case, the electrode is insulated all over.

Examples of an insulating material which can be used in the present invention include a glass-like resin, a polyimide resin (Japanese Patent Application No. 2-185249) and a low-viscosity insulating resin oligomer such as a silicone resin or an oligomer thereof and a methylmethacrylic resin or an oligomer thereof. When the composite electrode is used in an organic solvent, a glass matter coating film is necessary.

The insulating film can be formed by protecting the working electrode portion so that the insulating material may not adhere to this portion; or immersing the electrode in the insulating material so that the working electrode portion may not be immersed therein, and then allowing the excess insulating material to spontaneously drop; or when the thin film is desired, spin-coating the electrode and then curing the used resin in a suitable curing process.

Alternatively, the formation of the insulating film can be achieved by subjecting an insulating material such as an oxide of silica, alumina or zirconia to a dry method such as a vapor deposition method, a sputtering method and a chemical vapor deposition method.

Next, a silver film for the reference electrode is formed on the insulating film. The formation of the silver film can be achieved by any one of many known technique such as (1) a vapor deposition method, (2) a sputtering method, (3) plating and (4) an non-electrolytic plating process.

Here, a part of the silver layer formed on the insulating film of the electrode is electrochemically changed to silver chloride in a potassium chloride solution or the like.

At this time, a short lead wire is attached, by a silver paste or the like, to a silver exposure portion of the silver-silver chloride electrode formed on the insulating film, whereby conduction is accomplished. The attached portion is insulated with an insulating silicone adhesive or the like.

The thus prepared reference micro-electrode is compared with a reliable saturated calomel electrode (SCE) in a saturated potassium chloride solution to confirm a potential of the reference micro-electrode. Since a potential difference with this SCE is 42 millivolts at 25° C., a potential difference with the prepared reference micro-electrode is suitably in the range of ±10 millivolts of this value.

In the case that the reference electrode is used in materials such as an organism which tends to be poisoned by silver, the following procedure is recommended. The composite electrode with this reference electrode is placed in a thin glass tube or plastic tube, and the tip of the tube is narrowed down. Afterward, a potassium chloride solution is introduced into the tube, and the thus treated electrode is then used.

Next, in order to obtain the working electrode with the reference electrode and the counter electrode from the above-mentioned composite electrode, the counter electrode is necessary. The preparation process of this counter electrode will be described.

As in the case that the electrode is used at the position which is liable to be poisoned by silver, the working electrode with the reference electrode is placed in thin glass tube or a plastic tube, and the tip of the tube is narrowed down. Afterward, a potassium chloride solution is introduced into the tube, or the composite electrode is coated with an insulating film. A line of a metal, an alloy or carbon is wound on this tube or the insulating film. Alternatively, a metallic layer is formed thereon in the same manner as mentioned above, i.e., by a vapor deposition method, a sputtering method or the like, and a lead wire is connected to form the counter electrode.

EXAMPLES

The present invention will be described in detail in reference to examples, but the scope of the present invention should not be limited to these examples.

Example 1

As a working electrode of a composite electrode, a platinum wire was used, and this wire was then coated with a glass-like resin (Showa Denko K. K.; Glass-like Resin GR-100). Afterward, silver-silver chloride was attached on the coated layer, and it was then covered with a glass tube. A potassium chloride solution was introduced into this glass tube, and a platinum counter electrode was attached to the outer periphery of the tube to form the working electrode with a reference electrode and a counter electrode.

The platinum wire which was here used was 0.3 mm in diameter and 50 mm in length. This platinum wire was immersed in a 25% glass-like resin-ethanol solution except a portion which would be the working electrode, and the excess solution adhering on the platinum wire was allowed to spontaneously drop. After natural drying, temperature rise was carried out in an electric furnace until 180° C. had been reached, and the platinum wire was then heated for about 2 hours to cure the resin. One resin coating film often results in poor insulation. Therefore, the platinum wire was coated with the resin several times, and insulating properties were then confirmed. When a concentrated resin-ethanol solution was used instead of repeating the coating operation, cracks tend to occur at the time of curing. The sufficiently insulated platinum wire was immersed into a 0.5M silver nitride solution except the working electrode portion, and silver was deposited on the insulating resin film at −0.3 volt. A part of the silver-deposited portion was immersed into a 1M potassium chloride solution, and silver chloride was slowly deposited thereon at 0.34 V by the use of a saturated calomel electrode (SCE) as a reference electrode, thereby forming a composite micro-electrode. The constitutional view of this composite micro-electrode is shown in FIG. 1.

A potential of this composite electrode was measured versus the SCE. At this time, a potential difference was 48 mV, and this value was in the above-mentioned range, by which it was estimated that the sufficient composite electrode was prepared.

Example 2

Figure 2A:
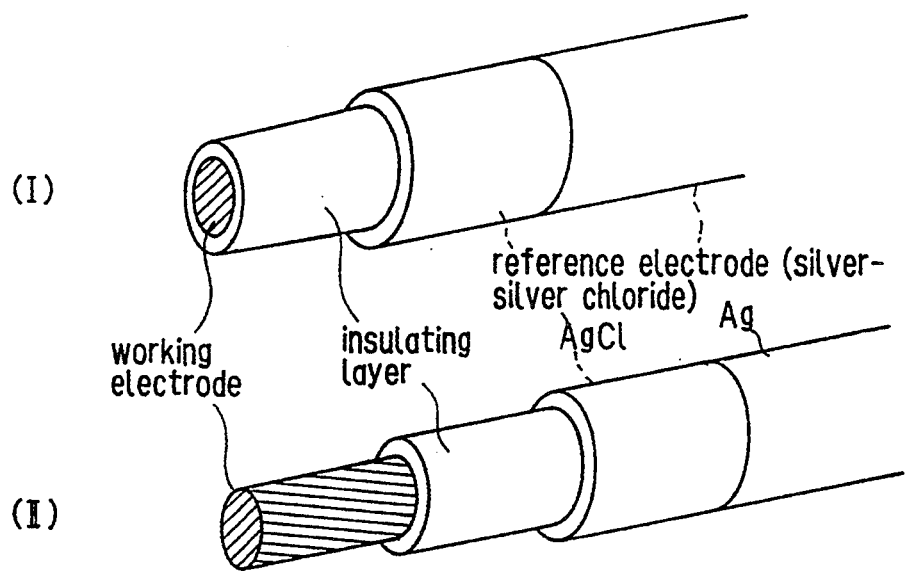
Figures 2A and 2B are constitutional views of a composite electrode obtained by forming the silver-silver chloride reference electrode on an insulating film of the working electrode comprising a carbon electrode thin micro-wire (0.1 mm$\phi$). In the composite electrode (I or I'), an edge surface is the working electrode and in a composite electrode (II or II'), the edge surface and a side surface are the working electrodes.
Figure 2B:
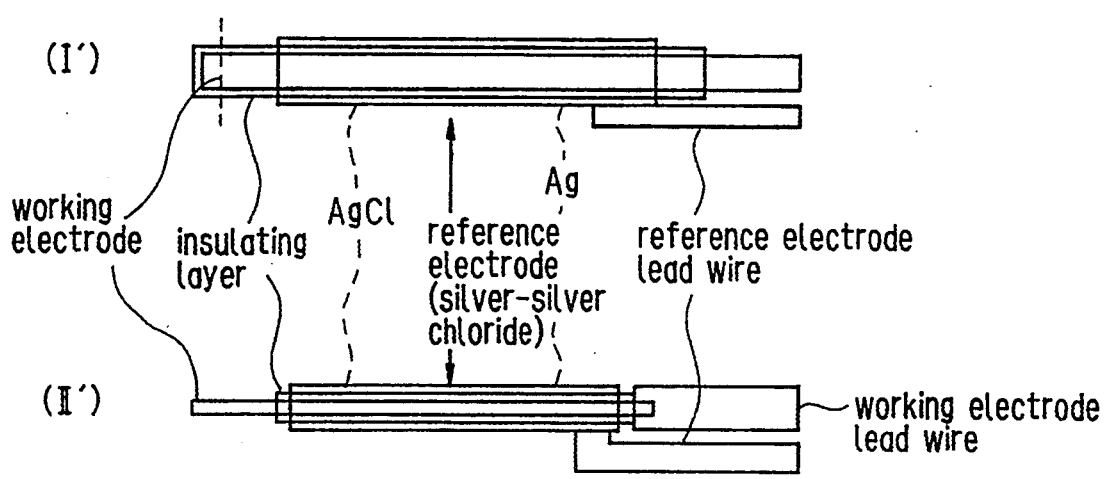

Next, a working electrode comprising a carbon thin wire with a reference electrode was prepared. The carbon thin wire which was used herein was 0.1 mm in diameter and 50 mm in length. This carbon thin wire was immersed into a low-viscosity silicone resin solution (made by The Shin-Etsu Chemical Co., Ltd.; Shin-Etsu Silicone KE441T) except a portion thereof which would be the working electrode, and the excess solution adhering on the carbon thin wire was allowed to spontaneously drop. After natural drying and curing, the sufficiently insulated carbon thin wire was placed in a sputter, and silver was deposited on the insulating film, the working electrode portion being covered with an aluminum foil or the like. A part of the silver-deposited portion was immersed into a 1M potassium chloride solution, and silver chloride was slowly deposited thereon at 0.34 V by the use of the SCE as a reference electrode. The constitutional view of the thus prepared composite micro-electrode is shown in FIG. 2.

A potential of this composite electrode was measured on the basis of the SCE. At this time, a potential difference was 49 mV, and this value was in the above-mentioned range, by which it was estimated that the sufficient composite electrode was prepared. FIG. 4 shows a current/potential curve in a 1M potassium chloride −0.005M potassium ferrocyanide solution by the use of the composite electrode. When the reference electrode according to the present invention was used, an oxidation-reduction potential of the above-mentioned ferrocyanide ions on the working electrode was 0,225 V, and a potential difference of 20 mV was shown in comparison with 0.245 V in the case of the SCE. This potential difference was evaluated to be a normal potential difference in a 1M potassium chloride solution.

Example 3

A concentric disk surface type composite micro-electrode which was disposable and in which a carbon thin wire was used as a working electrode with a reference electrode was prepared. This carbon thin wire used herein was 0.1 mm in diameter and 50 mm in length, and an insulating film was formed in the same manner as in Example 2. This carbon thin wire was placed in a sputter, and silver was deposited on the insulating film. One side of this silver layer was insulated in the same manner as in Example 2, and the uninsulated portion was changed to a silver chloride film in the same manner as in Example 2 or the whole surface film of the silver film was only changed to a silver chloride film. Finally, the electrode was entirely insulated to prepare a concentric disk surface type composite micro-electrode.

Figure 3:
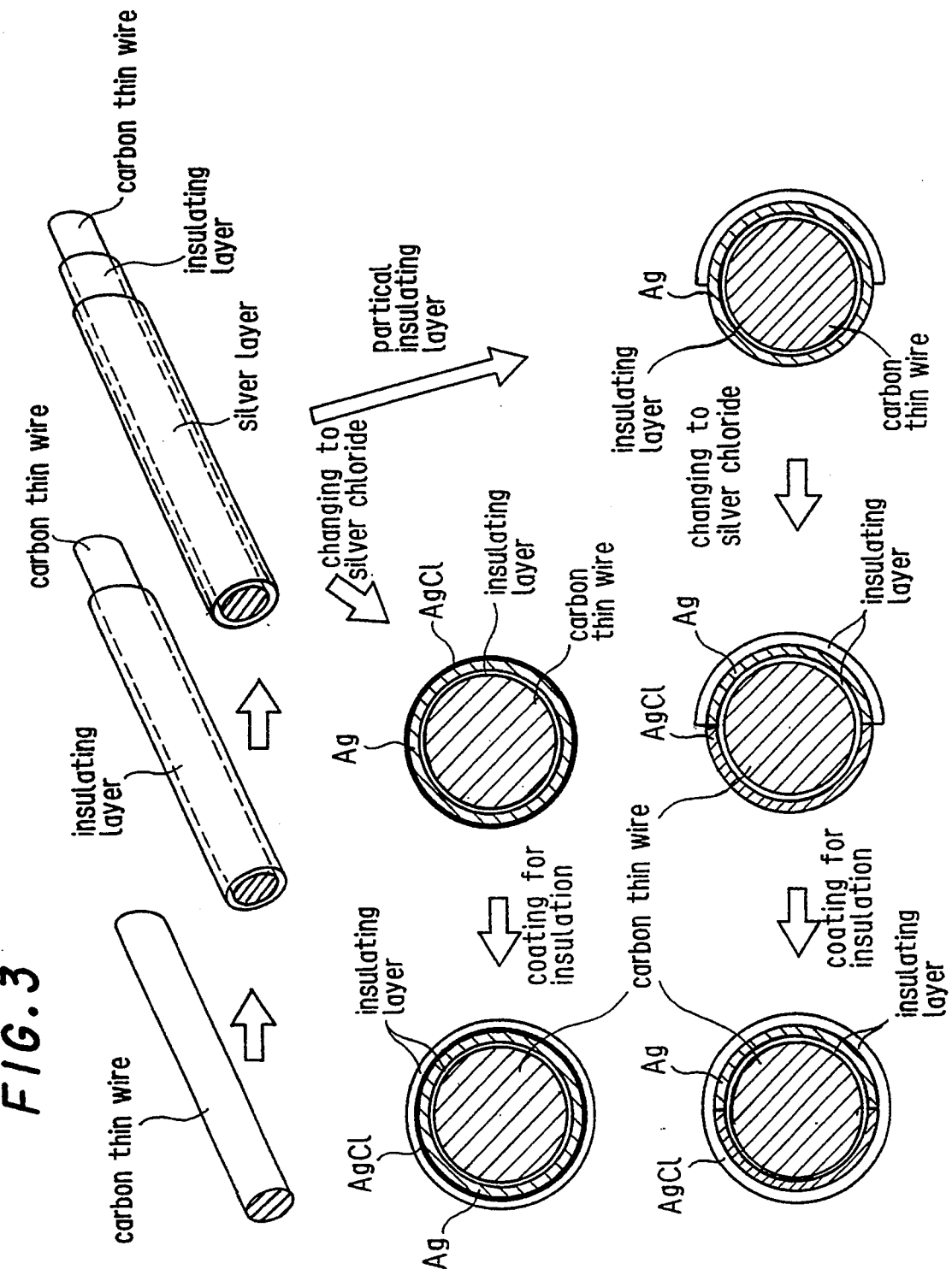
FIG. 3 is a constitutional view of a concentric disk surface type composite micro-electrode in which the carbon electrode of thin micro-wire is the working electrode.

FIG. 3 shows the constitution of the thus prepared concentric disk surface type composite micro-electrode.

A potential of this composite electrode was measured versus the SCE. At this time, a potential difference was 49 mV, by which it was estimated that the sufficient composite electrode was prepared.

Example 4

An iron EDTA compound similar to a peroxidase was introduced under heating or reduced pressure into micro-pores formed for a porous carbon working electrode having a diameter of 0.5 mm and a length of 60 mm, thereby forming a sensor electrode. Afterward, the sensor electrode was coated with a polyimide resin (made by Chisso Corporation; Polyimide PSI-N-6001), and after sufficient drying and curing, a silver film was formed on an insulating portion by an non-electrolytic plating process. A part of the silver-deposed portion is immersed into a 1M potassium chloride solution, and silver chloride was slowly deposited thereon at 0.34 V versus SCE as a reference electrode.

A potential of the thus prepared composite electrode was measured versus the SCE. At this time, a potential difference was 45 mV, and this value was in the above-mentioned range, by which it was estimated that the sufficient composite electrode was prepared.

In the present invention, the formation of the thin working electrode permits various measurements in micro-regions and of trace amount of samples, but heretofore, even if the thin working electrode is made, the merit of the micro-electrode has not been sufficiently utilized, since a reference electrode and a counter electrode have been thick.

However, the composite micro-electrode having the thin reference electrode and the thin counter electrode of the present invention can solve this problem and can facilitate experiments in which a micro-electrode is necessary.

Since an inexpensive electrode material such as carbon can be used, the working electrode may be constituted to be disposable. Even if it is not disposable, a new electrode surface can be repeatedly obtained by cutting off the used portion after once used. Therefore, the composite electrode of the present invention is very economical.

What is claimed is:

1. A renewable working micro-electrode with a reference micro-electrode comprising a working micro-electrode comprised of a micro-porous composite carbon thin wire or thin plate prepared by a highly dispersed composite composition comprised of a crystalline carbon fine powder and an organic binder, being extruded and said extruded material being calcined in an inert atmosphere or a non-oxidizing atmosphere, and a reference micro-electrode comprising an insulating material with which said working micro-electrode is coated except a working electrode portion, a silver coating layer on said insulating layer and a silver chloride layer deposited on a part of said silver layer.

2. A working micro-electrode with a reference micro-electrode according to claim 1, wherein said crystalline carbon fine powder is selected from the group consisting of graphite whisker, highly oriented pyrolytic graphite, Kish graphite, natural graphite and artificial graphite.

3. A working micro-electrode with a reference micro-electrode according to claim 1, wherein said organic binder is comprised of an organic compound which leaves a carbonized carbon when calcined in an inert atmosphere or a non-oxidizing atmosphere, said organic compound selected from the group consisting of an organic polymer, its monomer or oligomer, a tar, a pitch, a thermoplastic resin and an initial polymer of a thermosetting resin.

4. A working micro-electrode according to claim 3, wherein said pitch is a carbonized pitch.

5. A working micro-electrode with a reference micro-electrode according to claim 1, wherein said insulating material is selected from the group consisting of a silicon resin, a polyamide resin, and a methacrylic resin.

6. A working micro-electrode with a reference micro-electrode according to claim 1, wherein said insulating material comprises an oxide insulation material containing glass.

7. A working micro-electrode with a reference micro-electrode according to claim 1, wherein said reference micro-electrode comprises an insulating material or a reacting substance impregnated in carbon micro-pores extending to its interior and to a surface of said micro-electrode, said insulating material coating an outside surface of said micro-electrode, wherein a silver coats at least part of said insulation coating and a silver chloride is deposited on a part of said silver coating.

8. A working micro-electrode with a reference micro-electrode according to claim 7, wherein said insulating material impregnated in the micro-pores of said working micro-electrode is selected from a group consisting of silicone oil, a glass-like resin, and a polyimide resin.

9. A working micro-electrode with a reference micro-electrode according to claim 7, wherein said reacting substance impregnated in the micro-pores of said working electrode is selected from a group consisting of an enzyme, a metal complex compound, an organic compound, and a metabolite.

* * * * *